_ US009471980B2

United States Patent
Liu et al.

(10) Patent No.: US 9,471,980 B2
(45) Date of Patent: Oct. 18, 2016

(54) IMAGE PROCESSING APPARATUS, IMAGE PROCESSING METHOD THEREOF, AND IMAGE PROCESSING SYSTEM THEREOF

(71) Applicant: SAMSUNG ELECTRONICS CO., LTD., Suwon-si (KR)

(72) Inventors: Qin Liu, Gwonseon-gu (KR); Eung-bum Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 99 days.

(21) Appl. No.: 14/459,873

(22) Filed: Aug. 14, 2014

(65) Prior Publication Data

US 2015/0110246 A1 Apr. 23, 2015

(30) Foreign Application Priority Data

Oct. 18, 2013 (KR) .................. 10-2013-0124928

(51) Int. Cl.
*A61B 6/00* (2006.01)
*G06T 7/00* (2006.01)
*G06T 5/50* (2006.01)

(52) U.S. Cl.
CPC ............. *G06T 7/0026* (2013.01); *A61B 6/461* (2013.01); *A61B 6/483* (2013.01); *G06T 5/50* (2013.01); *G06T 7/0028* (2013.01); *A61B 6/4441* (2013.01); *A61B 6/467* (2013.01); *A61B 6/5247* (2013.01); *A61B 6/542* (2013.01); *G06T 2207/10116* (2013.01); *G06T 2207/20216* (2013.01)

(58) Field of Classification Search
CPC .. G01N 23/04; G01N 23/203; G01N 23/201; G06T 2207/10116
See application file for complete search history.

(56) References Cited

U.S. PATENT DOCUMENTS 6,665,373 B1 * 12/2003 Kotowski ............. G01N 23/20
378/57
8,107,589 B2 1/2012 Sakurai et al.
2012/0314842 A1 12/2012 Kargar et al.

FOREIGN PATENT DOCUMENTS

JP 2006-34452 A 2/2006
JP 2009-148494 A 7/2009
WO 2012/158106 A1 11/2012

OTHER PUBLICATIONS

Communication issued on Oct. 8, 2015 by the Korean Intellectual Property Office in related Application No. 10-2013-0124928.
Communication dated Apr. 25, 2016 issued by the Korean Intellectual Property Office in counterpart Korean Patent Application No. 10-2013-0124928 English Translation.

* cited by examiner

*Primary Examiner* — Hoon Song
(74) *Attorney, Agent, or Firm* — Sughrue Mion, PLLC

(57) ABSTRACT

The image processing apparatus includes a receiver for receiving a first image acquired by photographing scattered radiation of X-rays existing in a closed space and a second image acquired by photographing the closed space; and an image processor for generating a third image by combining the first image and the second image.

20 Claims, 10 Drawing Sheets

IMAGE PROCESSING APPARATUS, IMAGE PROCESSING METHOD THEREOF, AND IMAGE PROCESSING SYSTEM THEREOF

CROSS-REFERENCE TO RELATED APPLICATION

This application claims priority from Korean Patent Application No. 10-2013-0124928, filed on Oct. 18, 2013, in the Korean Intellectual Property Office, the disclosure of which is incorporated herein in its entirety by reference.

BACKGROUND

1. Field

One or more exemplary embodiments relate to displaying an amount of scattered radiation generated during X-ray radiographic imaging.

2. Description of the Related Art

A radiographic image processing apparatus detects abnormalities in a human body by using radiation. Examples of the medical imaging devices using radiation may include X-ray apparatuses that acquire an X-ray image by irradiating X-rays to a portion of the human body.

The X-ray apparatuses are widely used in chest imaging, abdomen imaging, skeleton imaging, nasal sinuses imaging, neck soft tissue imaging, and breast imaging.

Referring to FIG. 1, an X-ray apparatus 20 is disposed in a radiation lab 10.

The X-ray apparatus 20 generates and irradiates X-rays to a patient 11 located on a table 21. The X-ray apparatus 20 senses X-rays passing through the patient 11 and transmits a sensed X-ray signal to a workstation 30.

The workstation 30 receives a command to manipulate the X-ray apparatus 20 and controls the operations of the X-ray apparatus 20. FIG. 1 illustrates that the workstation 30 is disposed to be spaced apart from the X-ray apparatus 20.

Although the irradiation range of X-rays of an X-ray apparatus is limited by using the collimator, generation of scattered radiation caused by collision between X-rays and the objects or other substances is unavoidable. The scattered radiation spreads across a space in which the X-ray apparatus is located.

The patient who is subjected to the radiographic examination and users, such as medical radiation technologists, doctors, or nurses, are exposed to the scattered radiation, which may have harmful effects on the human body.

However, the X-rays and the scattered radiation are not visible to humans, and, thus, the users cannot know even when a large amount of scattered radiation is generated.

SUMMARY

Exemplary embodiments may address at least the above problems and/or disadvantages and other disadvantages not described above. However, exemplary embodiments are not required to overcome the disadvantages described above, and may not overcome any of the problems described above.

One or more exemplary embodiments relate to image processing apparatuses to allow a user to easily and quickly recognize an amount of scattered radiation generated during X-ray radiography, image processing methods thereof, and image processing systems thereof.

More particularly, one or more exemplary embodiments relate to image processing apparatuses to allow a user to easily and quickly recognize a distribution of scattered radiation and an amount of scattered radiation generated during X-ray radiography, image processing methods thereof, and image processing systems thereof.

According to one or more exemplary embodiments, an apparatus for processing an image includes: a receiver for receiving a first image acquired by photographing scattered radiation of X-rays existing in a space and a second image acquired by photographing the space; and an image processor for generating a third image by combining the first image and the second image.

The image processor may generate the third image by combining the first image and the second image by matching corresponding points in the space.

The apparatus may further include a display to display the third image.

The apparatus may further include an X-ray sensor for measuring an amount of scattered radiation at a position of the space and transmitting information regarding the amount of scattered radiation to the receiver.

The image processor may estimate an absolute value of the amount of scattered radiation in at least one region of the space by using the information regarding the amount of scattered radiation and the first image, and generate the third image to indicate the estimated absolute value in the third image.

The image processor may generate the third image by differently marking a first region having an amount of scattered radiation greater than a reference value in the space from a second region other than the first region based on the estimated absolute value.

The image processor may determine whether a first region having an amount of scattered radiation greater than a reference value exists in the space based on the estimated absolute value and output at least one of an image and a voice informing about the existence of the first region.

The apparatus may further include: a first camera acquiring the first image; and a second camera acquiring the second image.

According to one or more exemplary embodiments, a method of processing an image includes: receiving a first image acquired by photographing scattered radiation of X-rays existing in a space; receiving a second image acquired by photographing the space; and generating a third image by combining the first image and the second image.

The generating of the third image may include generating the third image by combining the first image and the second image by matching corresponding points in the space.

The method may further include displaying the third image.

The method may further include measuring an amount of scattered radiation at a position in the space.

The generating of the third image may include estimating an absolute value of the amount of scattered radiation in at least one region of the space by using the measured amount of the scattered radiation and the first image, and generating the third image to indicate the estimated absolute value in the third image.

The generating of the third image may include generating the third image by differently marking a first region having an amount of scattered radiation greater than a reference value in the space from a second region other than the first region based on the estimated absolute value.

The method may further include: determining whether a first region, in which the amount of scattered radiation exceeds a reference value, exists in the space based on the estimated absolute value; and outputting at least one selected from the group consisting of an image and a voice informing about the existence of the first region upon determination that the first region exists.

According to one or more exemplary embodiments, a system for processing an image includes: an X-ray apparatus disposed in a space, irradiating X-rays to an object, and acquiring an X-ray image corresponding to the X-rays; an X-ray camera photographing scattered radiation of X-rays existing in the space; a camera photographing the space; an image processor generating a third image by combining a first image acquired by the X-ray camera and a second image acquired by the camera; and a display displaying the third image.

BRIEF DESCRIPTION OF THE DRAWINGS

The above and/or other aspects will become more apparent by describing in detail certain exemplary embodiments, with reference to the accompanying drawings, in which.

DETAILED DESCRIPTION

Figure 1:
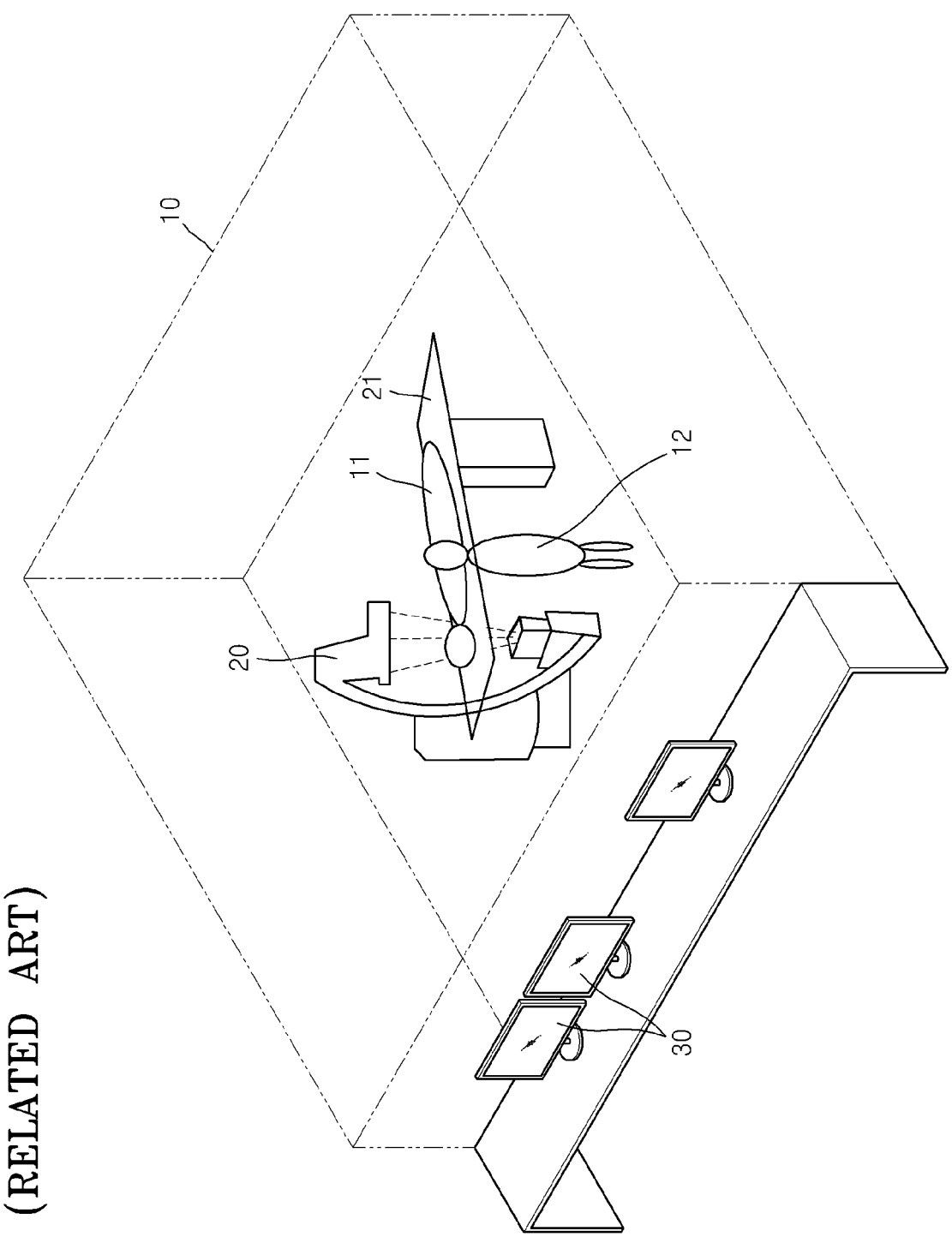
FIG. 1 is a diagram for describing radiography.

Certain exemplary embodiments are described in greater detail below with reference to the accompanying drawings.

In the following description, same reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, functions or elements known in the related art are not described in detail since they would obscure the exemplary embodiments with unnecessary detail.

Expressions such as "at least one of," when preceding a list of elements, modify the entire list of elements and do not modify the individual elements of the list.

In the present specification, an "image" may denote multi-dimensional data configured by discrete image elements (for example, pixels in a two-dimensional (2D) image and voxels in a three-dimensional (3D) image). For example, an image may include medical images of an object acquired by using X-rays, computerized tomography (CT), magnetic resonance imaging (MRI), ultrasound waves, and other medical image systems.

Also, in the present specification, an object may include a human being or an animal, or a part of the human being or the animal. For example, the object may include organs, such as the liver, the heart, the uterus, the brain, breasts, the abdomen, or blood vessels. Also, the "object" may include a phantom. The phantom denotes a material having a volume, a density, and an effective atomic number that is nearly equivalent to those of a living organism, and a phantom according to exemplary embodiments may be a spherical phantom having similar properties to those of the human body.

In the present specification, a "user" is a medical expert, for example, a doctor, a nurse, a medical specialist, or a medical imaging expert, or an engineer managing medical apparatuses; however, this is not limiting.

Figure 2:
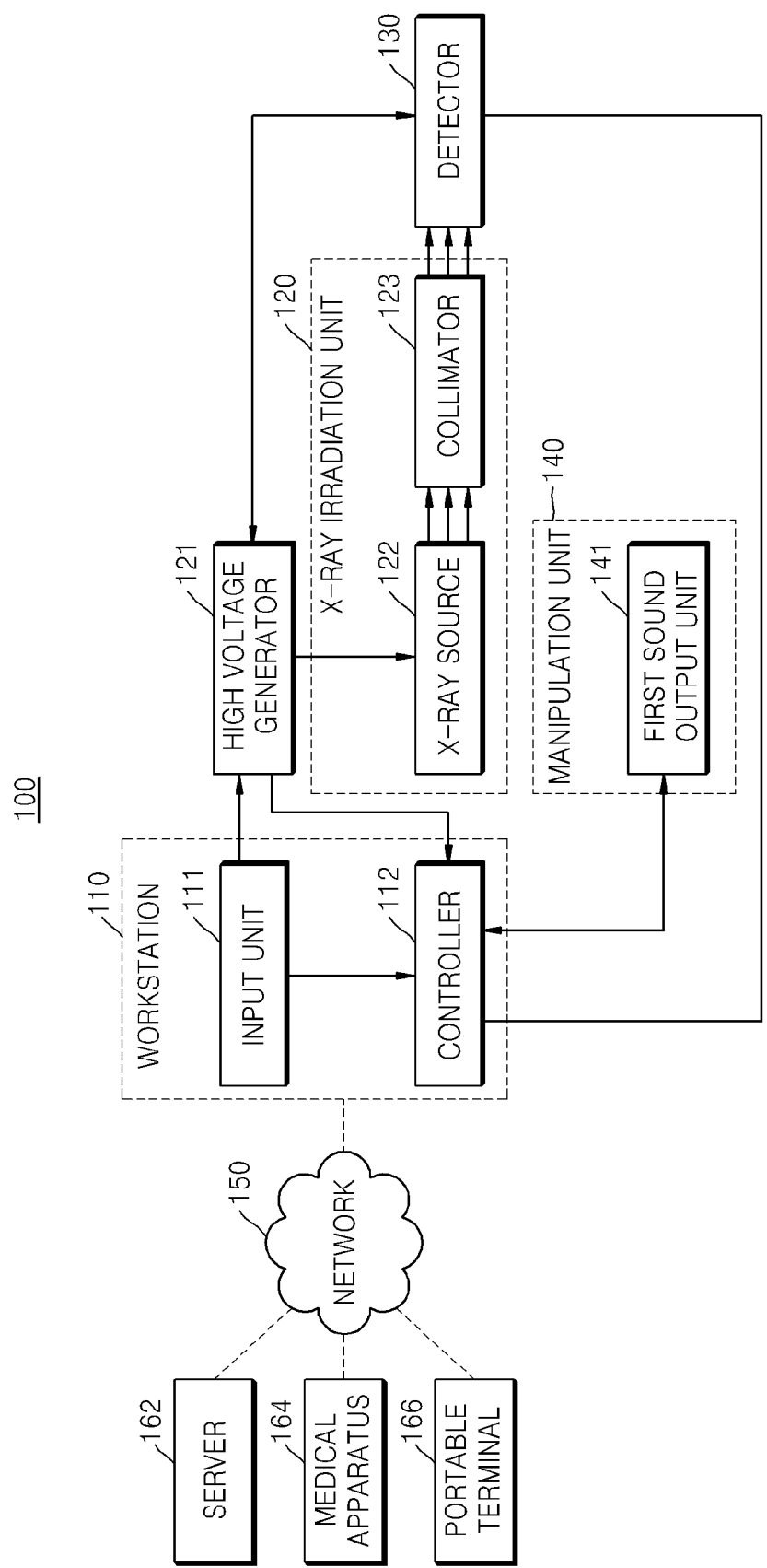
FIG. 2 illustrates an X-ray apparatus used in an exemplary embodiment.

FIG. 2 illustrates an X-ray apparatus 100 of an exemplary embodiment.

The X-ray apparatus 100 shown in FIG. 2 may be a fixed-type X-ray apparatus or a movable X-ray apparatus.

Referring to FIG. 2, the X-ray apparatus 100 includes a workstation 110, an X-ray irradiation unit 120, a high voltage generator 121, and a detector 130.

The workstation 110 includes an input unit 111 through which a user may input commands for manipulating the X-ray apparatus 100, and a controller 112 controlling operations of the X-ray apparatus 100.

The high voltage generator 121 generates a high voltage for generating X-rays, and applies the high voltage to an X-ray source 122.

The X-ray irradiation unit 120 includes the X-ray source 122 receiving the high voltage applied from the high voltage generator 121 to generate and irradiate X-rays, and a collimator 123 for guiding a path of the X-ray irradiated from the X-ray source 122.

The detector 130 detects the X-rays that are irradiated from the X-ray irradiation unit 120 and have been transmitted through the object.

The X-ray apparatus 100 may further include a manipulator 140 including a first sound output unit 141 outputting sound representing information relating to an imaging operation such as the X-ray irradiation under control of the controller 112.

The workstation 110, the X-ray irradiation unit 120, the high voltage generator 121, and the detector 130 may be connected to each other via wires or wirelessly. If they are connected to each other wirelessly, a device (not shown) for synchronizing clocks with each other may be further included.

The input unit 111 may include a keyboard, a mouse, a touch screen, a voice recognizer, a fingerprint recognizer, an iris recognizer, and the like, which are known to those skilled in the art. The user may input a command for irradiating the X-rays via the input unit 111, and to do this, the input unit 111 may include a switch for inputting the command. The switch may be configured so that an irradiation command for irradiating the X-rays may be input only when the switch is pressed twice.

That is, when the user presses the switch once, a prepare command for performing a pre-heating operation for X-ray irradiation may be input through the switch, and then, when the user presses the switch once more, the irradiation command for irradiating the X-ray may be input through the switch. When the user manipulates the switch as described above, the input unit 111 generates signals corresponding to the commands input through the switch manipulation, that is, a prepare signal and an irradiation signal, and outputs the generated signals to the high voltage generator 121 generating a high voltage for generating the X-rays.

When the high voltage generator 121 receives the prepare signal output from the input unit 111, the high voltage generator 121 starts a pre-heating operation, and when the pre-heating is finished, the high voltage generator 121 outputs a ready signal to the controller 112. The detector 130 also needs to prepare for detecting the X-rays, and thus, when the high voltage generator 121 receives the prepare signal output from the input unit 111, the high voltage generator 121 outputs a prepare signal to the detector 130 at the same time, so that the detector 130 may prepare for detecting the X-rays transmitted through the object. The detector 130 prepares for detecting the X-rays when receiving the prepare signal, and when the preparing for the detection is finished, the detector 130 outputs a ready signal to the high voltage generator 121 and the controller 112.

When the pre-heating operation of the high voltage generator 121 is finished, the detector 130 is ready to detect the X-rays, and the irradiation signal is output from the input unit 111 to the high voltage generator 121, the high voltage generator 121 generates and applies the high voltage to the X-ray source 122, which irradiates the X-rays.

When the irradiation signal is output from the input unit 111, the controller 112 may output a sound output signal to the first sound output unit 141 so that the first sound output unit 141 outputs a predetermined sound and the object may recognize the irradiation of X-rays. The first sound output unit 141 may output a sound representing other information related to the imaging, in addition to the X-ray irradiation. In FIG. 2, the first sound output unit 141 is included in the manipulator 140; however, an exemplary embodiment is not limited thereto, and the first sound output unit 141 may be located at a different location from the manipulator 140. For example, the first sound output unit 141 may be included in the workstation 110, or may be located on a wall surface of an examination room in which radiography of the object is performed.

The controller 112 controls locations of the X-ray irradiation unit 120 and the detector 130, an imaging timing, and photographing conditions according to photographing conditions set by the user.

The controller 112 controls the high voltage generator 121 and the detector 130 according to the command input via the input unit 111 so as to control an irradiation timing of the X-rays, an intensity of the X-rays, and an irradiation region of the X-rays. The controller 112 adjusts the location of the detector 130 according to a predetermined photographing condition, and controls an operation timing of the detector 130.

The controller 112 generates a medical image of the object by using image data received from the detector 130. In particular, the controller 112 receives the image data from the detector 130, and then, generates the medical image of the object by removing noise from the image data, and adjusting a dynamic range and interleaving of the image data.

The X-ray apparatus 100 shown in FIG. 2 may further include an output unit (not shown) for outputting the medical image generated by the controller 112. The output unit may output information that is necessary for the user to manipulate the X-ray apparatus 100, for example, a user interface (UI), user information, or object information. The output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a 3D display, a transparent display, and other various output devices known to those skilled in the art.

The workstation 110 shown in FIG. 1 may further include a communicator (not shown) that may be connected to a server 162, another medical apparatus 164, and a portable terminal 166 via a network 150.

The communicator may be connected to the network 150 via wires or wirelessly to communicate with the server 162, the medical apparatus 164, or the portable terminal 166. The communicator may transmit or receive data relating to diagnosis of the object via the network 150, and may transmit or receive medical images captured by another medical apparatus 164, for example, a CT, an MRI, or an X-ray apparatus. Moreover, the communicator may receive a medical history or treatment schedule of an object (e.g., a patient) from the server 162 to diagnose the object. The communicator may perform data communication with the portable terminal 166 such as a mobile phone, a personal digital assistant (PDA), or a laptop computer of a doctor or a patient, as well as the server 162 or the medical apparatus 164 in a hospital.

The communicator may include one or more elements enabling communication with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the exemplary embodiments are not limited thereto.

The wired communication module is a module for communicating by using an electric signal or an optical signal, and the wired communication technology may be wired communication technology using a pair cable, a coaxial cable, an optical fiber cable, or a wired communication technology that is well known in the art.

The wireless communication module may transmit/receive a wireless signal to/from at least one of a base, an external device, and a server in a mobile communication network. Here, the wireless signal may be a voice call signal, a video call signal, or various types of data according to text/multimedia messages transmission.

The X-ray apparatus 100 shown in FIG. 2 may include a plurality of digital signal processors (DSPs), an ultra-small calculator, and a processing circuit for specialized usage (for example, high speed analog/digital (A/D) conversion, high speed Fourier transformation, an array process, etc.).

The communication between the workstation 110 and the X-ray irradiation unit 120, between the workstation 110 and the high voltage generator 211, and between the workstation 110 and the detector 130 may use a high speed digital interface, such as low voltage differential signaling (LVDS), asynchronous serial communication, such as universal asynchronous receiver transmitter (UART), synchronous serial communication, or a low latency network protocol, such as a controller area network (CAN), and other various communication methods that are known to those skilled in the art may be used.

Figure 3:
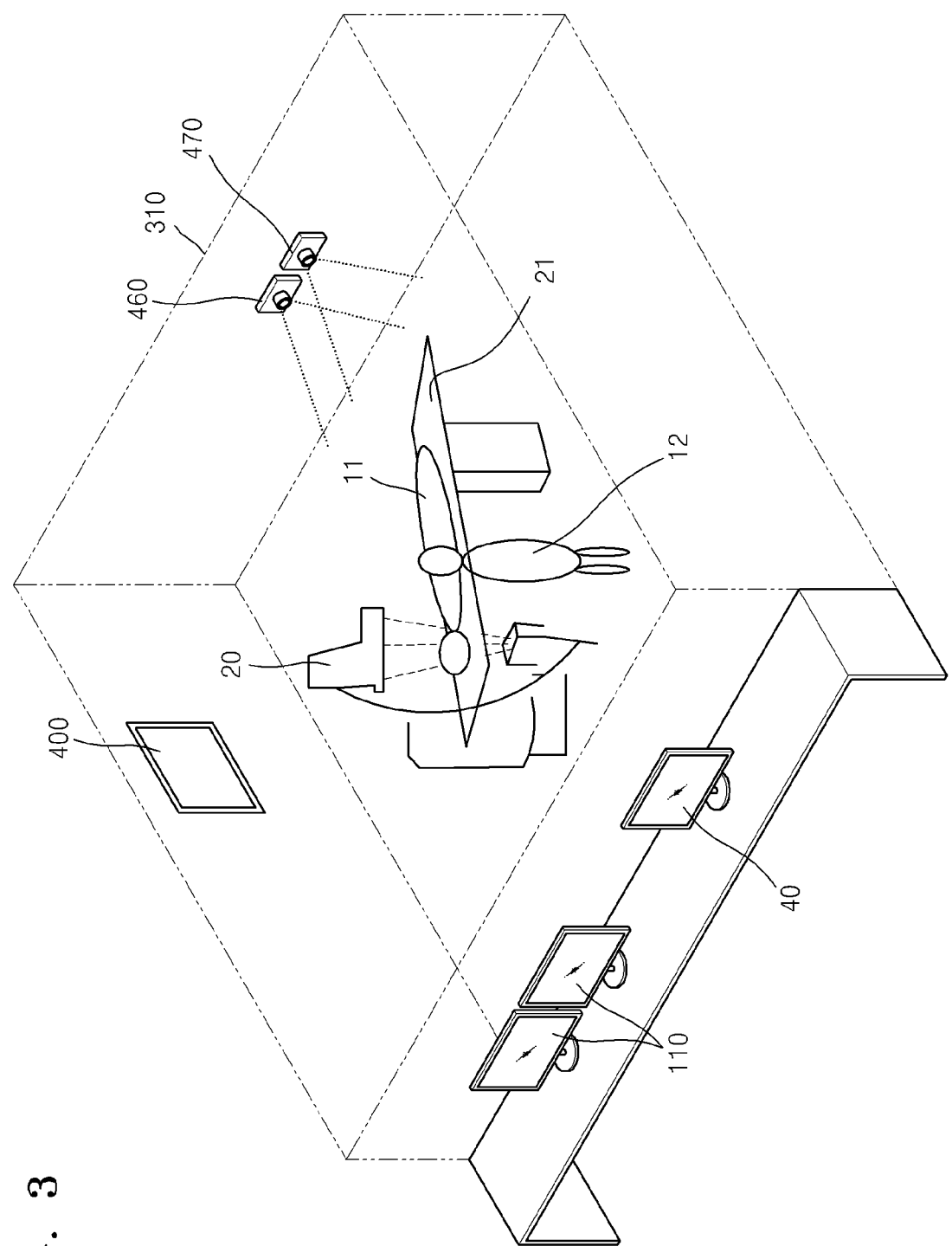
FIG. 3 is a diagram for describing an image processing apparatus according to an exemplary embodiment.

FIG. 3 is a diagram for describing an image processing apparatus 400 according to an exemplary embodiment.

The image processing apparatus 400 is an apparatus configured to allow the user to easily and quickly recognize scattered radiation generated during radiography and an amount of the scattered radiation.

The image processing apparatus 400 may be included into the controller 112 of the X-ray apparatus 100 or may be a separate device from the X-ray apparatus 100. FIG. 3 exemplarily illustrates that the image processing apparatus 400 is separately disposed from the X-ray apparatus 100 and includes a display.

Referring to FIG. 3, the image processing apparatus 400 may be disposed in a predetermined space in which the X-ray irradiation unit 120 is disposed. In this regard, the predetermined space refers to a space in which scattered radiation generated by X-rays irradiated from the X-ray irradiation unit 120 exists. The user 12 such as a doctor, a nurse, a medical specialist, and a medical imaging expert may manipulate the X-ray irradiation unit 120 in the predetermined space. For example, the predetermined space may be a radiation lab 310.

The image processing apparatus 400 may be disposed at a location where the user 12, who performs radiography in the radiation lab 310, may easily recognize the amount of scattered radiation existing in the radiation lab 310. FIG. 3 exemplarily illustrates that the image processing apparatus 400 is disposed on a wall of the radiation lab 310 such that an image is viewed by the user 12.

A first camera 460 to acquire an X-ray image within a predetermined space and a second camera 470 to acquire a general image of the predetermined space are disposed in the radiation lab 310, which is the predetermined space.

The first camera 460 and the second camera 470 may be disposed so as to photograph the entire area where scattered radiation may exist. FIG. 3 exemplarily illustrates that the first camera 460 and the second camera 470 are disposed on upper portions of a wall of the radiation lab 310 such that the radiation lab 310 is entirely photographed around the X-ray irradiation unit 120.

Figure 4:
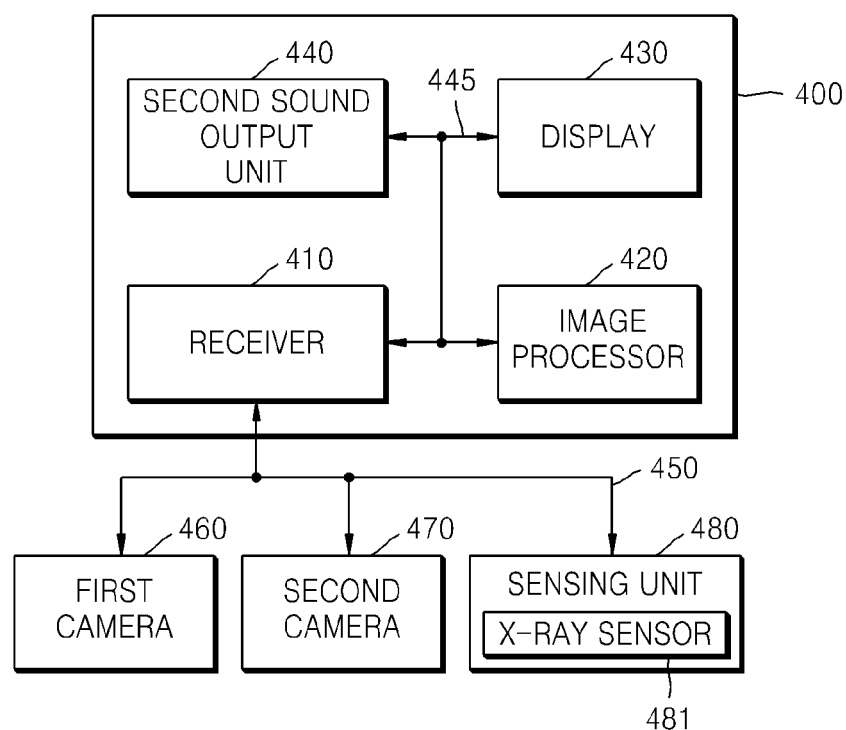
FIG. 4 is a block diagram of an image processing apparatus according to an exemplary embodiment.

FIG. 4 is a block diagram of an image processing apparatus 400 according to an exemplary embodiment. The descriptions of the elements illustrated in FIG. 4 which are the same as those given with reference to FIG. 3 will not be repeated here.

Referring to FIG. 4, the image processing apparatus 400 may include a receiver 410 and an image processor 420. The image processing apparatus 400 may further include at least one of a display 430 and a second sound output unit 440.

The elements of the image processing apparatus 400 are connected to one another via communication lines 445 in a wired or wireless manner, and transmission and reception of signals may be performed via the wired or wireless communication lines 445 within the image processing apparatus 400.

The receiver 410 receives a first image of scattered radiation generated by X-rays existing in a predetermined space and a second image that is a general image of the predetermined space which may be the radiation lab 310. The receiver 410 transmits the received first and second images to the image processor 420.

In particular, the receiver 410 is connected to the first camera 460 and the second camera 470 via a network 450 and receives the first image acquired by the first camera 460 and the second image acquired by the second camera 470.

Here, the network 450 is a wired or wireless communication network that enables data transmission and reception. The network 450 may be implemented by using various communication network standards such as local area network (LAN), wide area network (WAN), 3G, Long Term Evolution (LTE), Wireless LAN (WLAN, Wi-Fi), Wireless broadband (Wibro), code division multiple access (CDMA), wideband CDMA (WCDMA), and Near Field Communication (NFC).

The first camera 460 photographs scattered radiation generated by X-rays within the predetermined space.

In particular, the first camera 460 controls a grid in a direction toward scattered radiation, converts the scattered radiation existing in the predetermined space into visible light by using an image intensifier disposed therein, and senses the converted visible light by using a photoelectronic device, such as a charge coupled device (CCD) sensor or a complementary metal oxide semiconductor (CMOS) sensor. The first camera 460 generates an image by using the scattered radiation distributed in the predetermined space by using an amount of the sensed visible light.

In FIGS. 3 and 4, one first camera 460 is disposed in the radiation lab 310, which is a space to be photographed, but a plurality of first cameras may be used. In addition, a plurality of first images may also be acquired by moving the first camera 460. In this case, since the scattered radiation may be photographed at various angles, the user may recognize the distribution of the scattered radiation more accurately on a location basis.

The second camera 470 is used to acquire a general image by photographing the radiation lab 310. In the same manner as the first camera 460, a plurality of second cameras may also be disposed in the radiation lab 310. In addition, a plurality of second images may also be acquired by moving the second camera 470.

The image processor 420 generates a third image by combining the first image and the second image. When a plurality of the first and second images are received, a plurality of third images may be generated by combining respectively corresponding first and second images.

In addition, the second sound output unit 440 may output a sound in response to control by the image processor 420.

Figure 5:
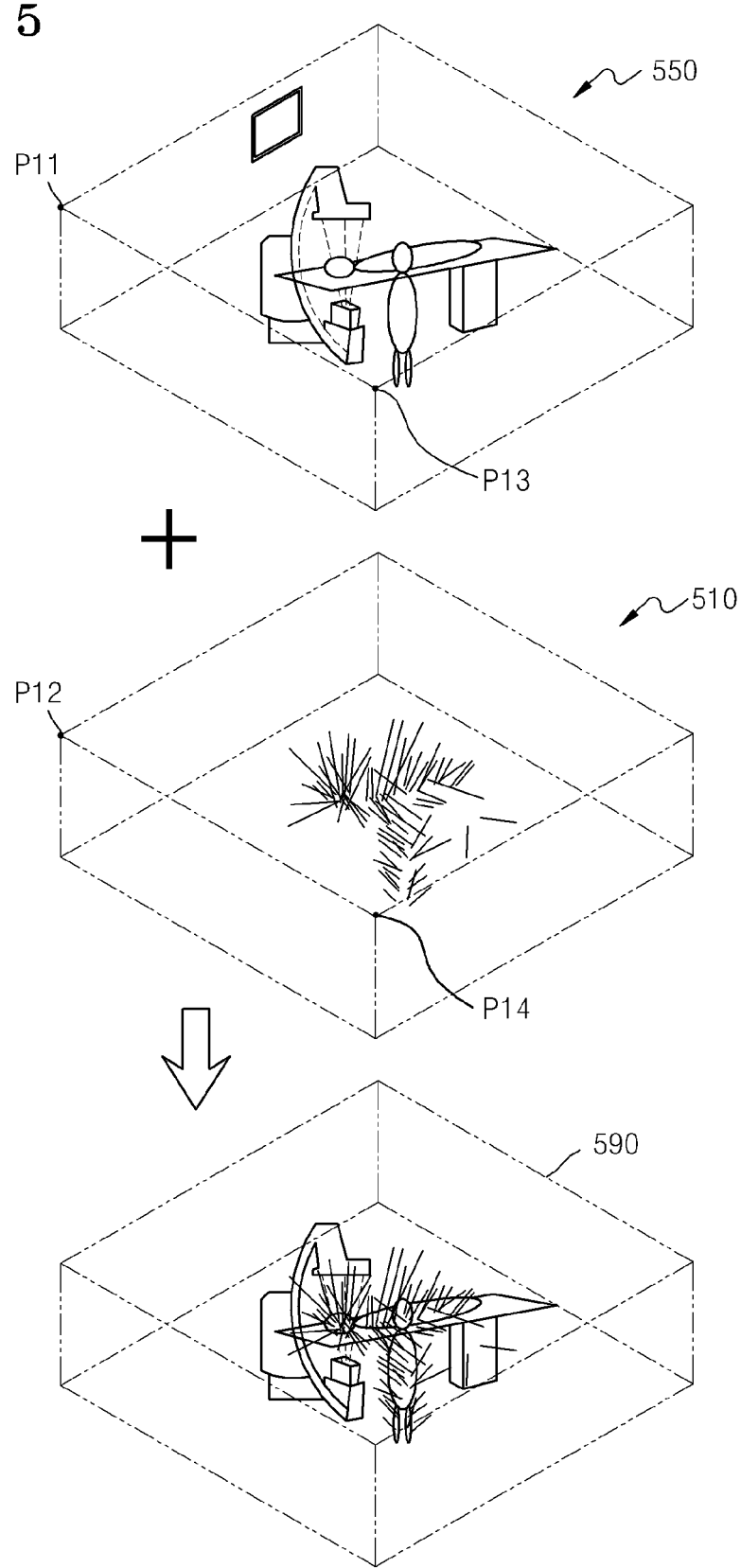
FIG. 5 is a diagram for describing generation of a third image.

FIG. 5 is a diagram for describing generation of a third image.

Referring to FIG. 5, the first camera 460 photographs scattered radiation existing in the radiation lab 310 to generate a first image 510. The first image 510 shows distribution of the scattered radiation 515.

The second camera 470 photographs the radiation lab 310 to create a general image, i.e., a second image 550.

The first camera 460 and the second camera 470 may simultaneously acquire the first image 510 and the second image 550.

The image processor 420 combines the first image 510 received from the first camera 460 and the second image 550 received from the second camera 470 to generate a third image 590.

The image processor 420 generates the third image 590 by combining the first image 510 and the second image 550 by matching the same points within a predetermined space. For example, referring to FIG. 5, the third image 590 may be generated by matching points indicating the same points, i.e., by matching a point P11 with a point P12 and matching a point P13 with a point P14. Although FIG. 5 illustrates the third image 590 as a 3D image, the third image may also be generated as a 2D image or a multi-dimensional image.

The image processing apparatus 400 may include a display 430 to display the third image 590. The display 430 may be located where the third image 590 is easily viewed by the user 12 within the predetermined space. For example, since the user 12 generally assists in acquiring an X-ray image of the patient 11 near the X-ray irradiation unit 120, the display 430 may be located at a front portion of the X-ray apparatus 100 where the user 12 is generally located as illustrated in FIG. 5.

The display 430 may be physically spaced apart from the other elements including the image processor 420, the receiver 410, and the second sound output unit 440. For example, the image processor 420, the receiver 410, and the second sound output unit 440 may be included in an external computer 40 or the workstation 110. In addition, when the image processing apparatus 400 does not include the display 430, the image processing apparatus 400 may transmit the third image 590 generated by the image processor 420 to a separate display device via a network.

The user 12 may easily recognize a place where a large amount of scattered radiation is generated and relative density of the scattered radiation by using the third image 590 displayed on the image processing apparatus 400. Accordingly, the user 12 may take action to block or avoid harmful radiation.

The image processing apparatus 400 may also include the sensing unit 480 which may be disposed independently from the image processing apparatus 400 and may transmit a sensing signal to the image processing apparatus 400.

The sensing unit 480 may include one or more X-ray sensors 481. The X-ray sensor 481 is disposed at a position of the predetermined space and senses an amount of scattered radiation at the position. For example, when the sensing unit 480 includes two X-ray sensors 481, one X-ray sensor may be attached to a side surface of the table 21 and the other X-ray sensor may be attached to a portion of the body of the user 12.

For example, the X-ray sensor 481 senses the amount of scattered radiation at predetermined intervals while the first camera 460 and the second camera 470 acquire images and transmits sensed information to the image processor 420 via the receiver 410.

The image processor 420 may receive the sensed information from the sensing unit 480 via the receiver 410 and estimate an absolute value of the scattered radiation distributed in the predetermined space by using the sensed information and the first image 510. In particular, the first image 510 shows the distribution and relative density of the scattered distribution. Thus, a relationship between the density of the scattered radiation and the absolute value of the amount of the scattered radiation may be estimated by matching the amount of the scattered radiation of a point included in the sensed information with the density of the scattered radiation existing at the point in the first image 510. Accordingly, the absolute values of the amounts of scattered radiation existing at the remaining area of the first image 510 may be predicted.

Thus, the image processor 420 may estimate the entire amount of the scattered radiation distributed in the predetermined space by using a small number of X-ray sensors 481.

The image processor 420 may generate the third image 590, which allows the user to recognize the absolute value of the amount of scattered radiation distributed in the predetermined space by using the estimated absolute value of the amount of the scattered radiation distributed in the first image 510, and display the third image 590.

Figure 6:
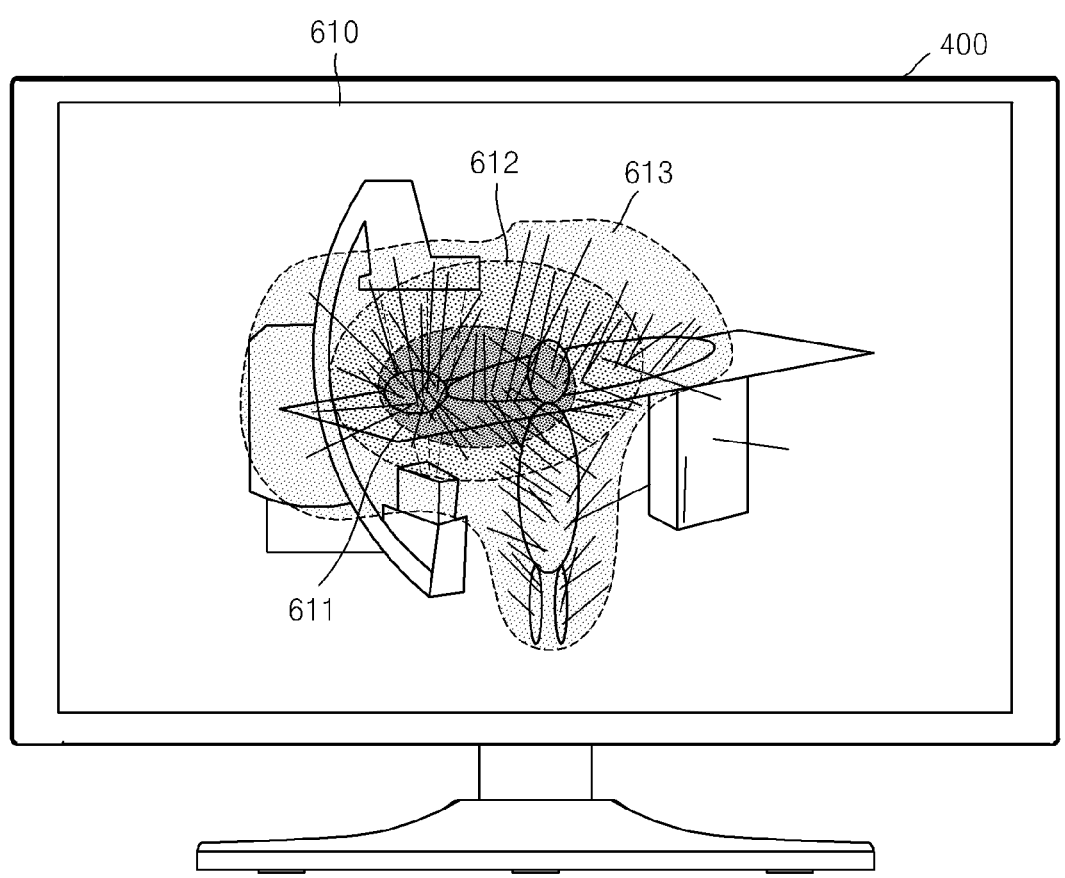
FIG. 6 is a diagram for describing an example of the third image.

FIG. 6 is a diagram for describing an example of the third image. Referring to FIG. 6, the image processing apparatus 400 displays a third image 610.

Referring to FIG. 6, the image processor 420 may generate the third image 610 in which a first region 611, in which an amount of scattered radiation existing within a predetermined space is greater than a reference value, is differently marked from a second region, which is the remaining area except for the first region 611, based on the estimated absolute value.

For example, the first region 611 may be marked by using slashes or a different color. Alternatively, the first region 611 may be highlighted. The first region 611 may also be marked by changing at least one of the shape and color of the scattered radiation.

In this regard, the reference value may be set differently in consideration of an age of the object to be radiographed, radiography time, and the like.

The image processor 420 may generate the third image 610 by differently marking regions, in which the amount of the scattered radiation does not exceed the reference value within the predetermined space, on a section basis in accordance to the absolute values of the amounts of the scattered radiation.

For example, when the reference value is set as 5 milligray (mGy), a region 612 having an estimated amount of scattered radiation of 4 to 5 mGy, with an exception of the first region 611 having an estimated amount of scattered radiation greater than 5 mGy, may be marked to be recognized by the user. In addition, a region 613 having an estimated amount of scattered radiation of 3 to 4 mGy may be marked to be recognized by the user. For example, the third image 610 may be generated and displayed by indicating the region 611 with red, the region 612 with orange, and the region 613 with yellow.

Figure 7:
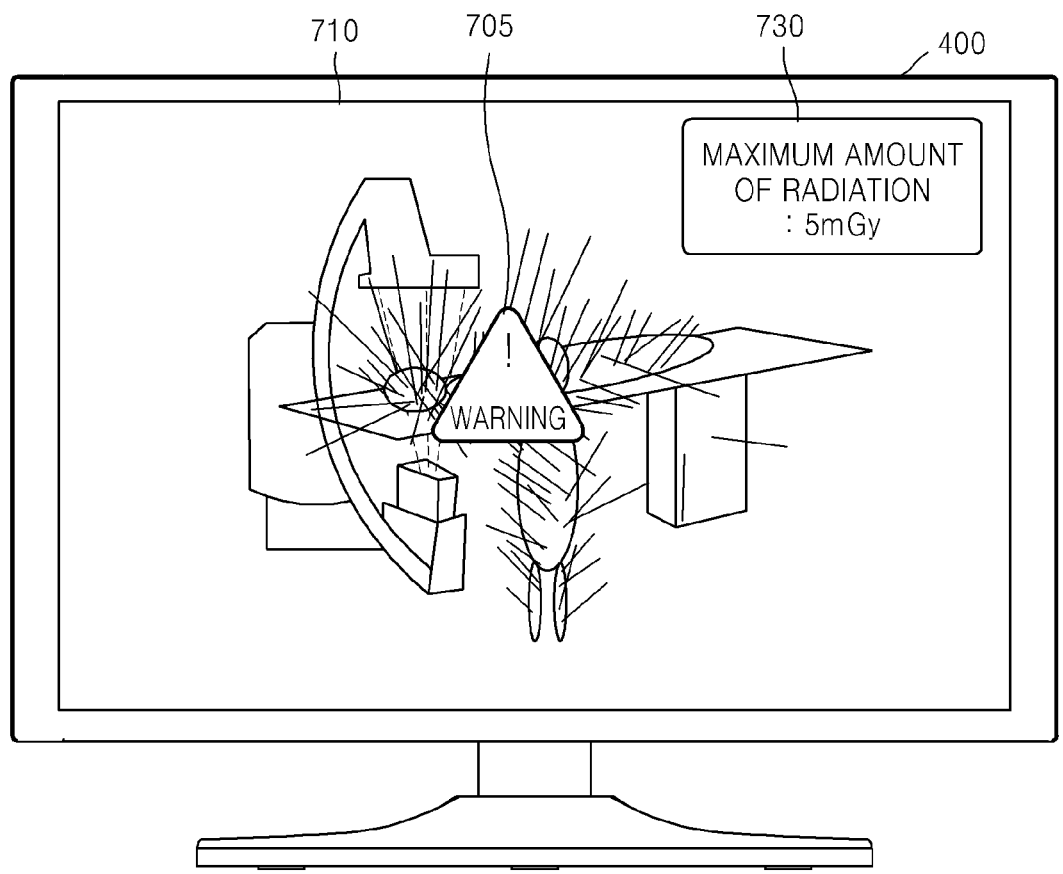
FIG. 7 is a diagram for describing another example of the third image.

FIG. 7 is a diagram for describing another example of the third image. Referring to FIG. 7, the image processing apparatus 400 displays a third image 710.

The image processor 420 determines whether a first region 705, in which the amount of scattered radiation exceeds the reference value, exists in the predetermined space based on the estimated absolute value. Upon determination that the first region 705 exists, an image or a voice indicating the existence of the first region 705 may be output.

Referring to FIG. 7, when the first region 705 having the amount of scattered radiation exceeding the reference value, exists, a warning 720 indicating the existence of the first region 705 may be displayed at the first region 705. In addition, a window 730 indicating the estimated amount of scattered radiation of the first region 705 may be displayed on the third image 710.

The image processor 420 may control the second sound output unit 440 to output a warning beep when there is a region having an amount of scattered radiation exceeding the reference value in the predetermined space.

Figure 8:
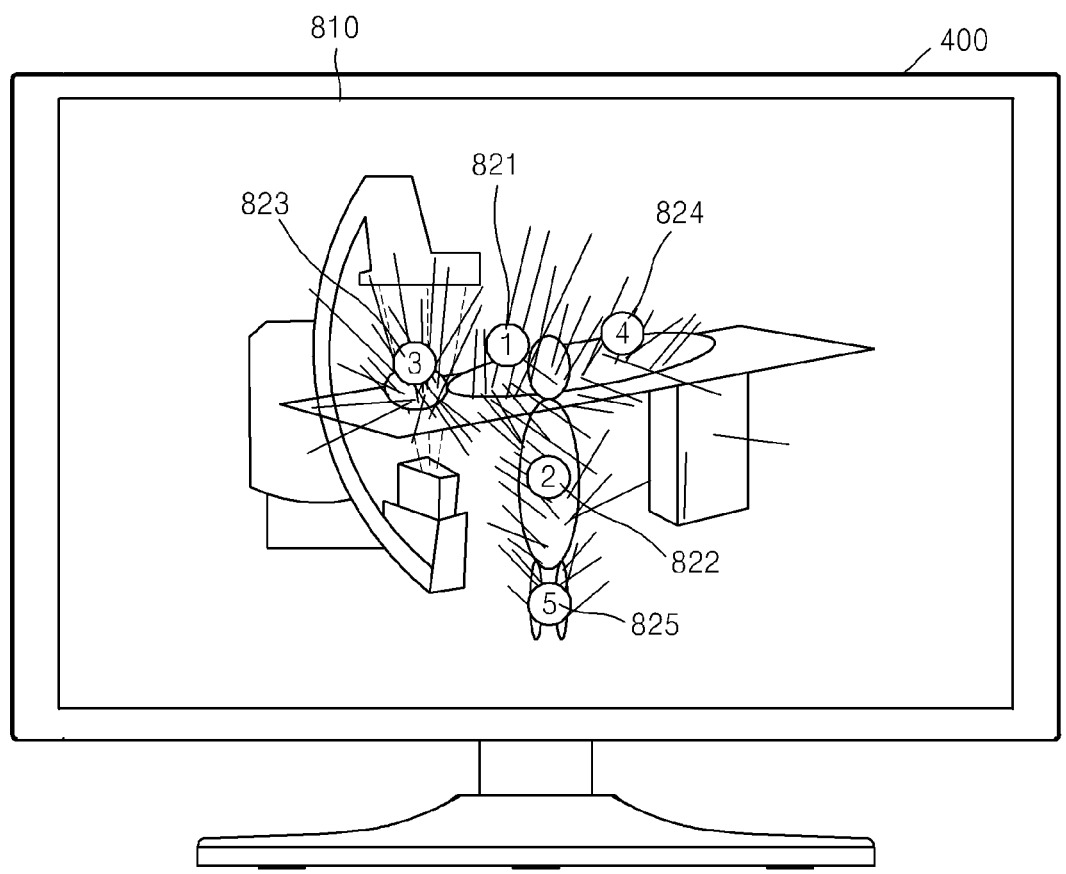
FIG. 8 is a diagram for describing another example of the third image.

FIG. 8 is a diagram for describing another example of the third image. Referring to FIG. 8, the image processing apparatus 400 displays a third image 810.

In particular, the image processor 420 may estimate an absolute value of scattered radiation distributed in the first image 510 by using an amount of scattered radiation measured by the sensing unit 480 and the first image 510, and may generate a third image 810 such that the estimated absolute value is indicated in the third image 810.

Referring to FIG. 8, the third image 810 may be displayed such that an estimated amount of scattered radiation of one or more points of the first image 510 is indicated. In more detail, estimated amounts of the scattered radiation may be indicated at a plurality of points 821, 822, 823, 824, and 825 of the third image 810.

Figure 9:
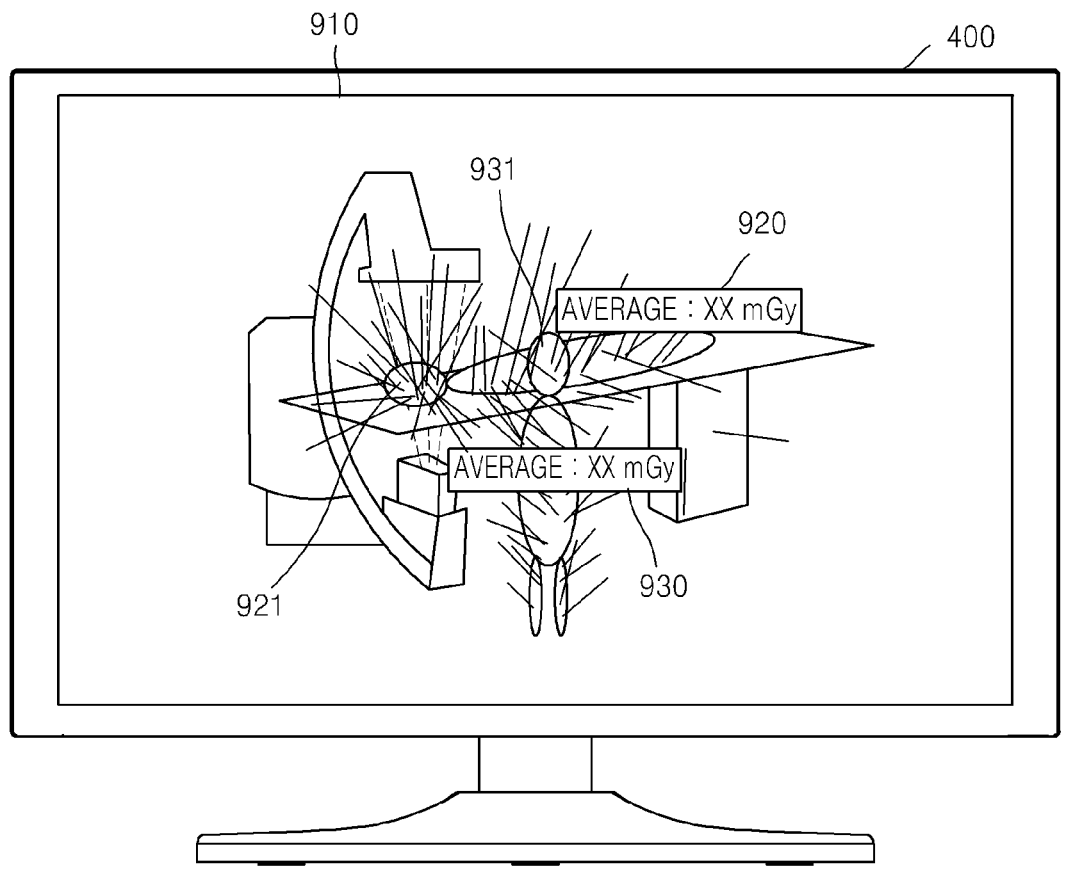
FIG. 9 is a diagram for describing another example of the third image.

FIG. 9 is a diagram for describing another example of the third image. Referring to FIG. 9, the image processing apparatus 400 displays a third image 910.

The image processor 420 may identify a user and a patient, estimate amounts of scattered radiation at locations of the identified user and the patient, and generate a third image 910 by displaying the estimated amounts of the scattered radiation at the locations of the user and the patient. The identification of the user or patient may be performed in the second image by recognizing people through image recognition.

The amounts of the scattered radiation at locations of the user and the patient may directly be measured by attaching the X-ray sensor 481 to at least one of the user and the patient. In this regard, the amounts of the scattered radiation applied to the user and the patient may be measured more accurately.

In addition, when the estimated or measured amounts of the scattered radiation at the locations of the user and the patient are greater than the reference value, the image processor 420 may also control the second sound output unit 440 or the display 430 to output a warning voice or video message.

Alternatively, the sensing unit 480 may further include an infrared sensor (not shown). In this case, the infrared sensor (not shown) may sense a human body, and the image processor 420 may receive the sensed information. In this case, the image processor 420 may obtain a region where a person is located by using the sensed information and estimate the amount of scattered radiation of the region by using the first image and the amount of scattered radiation of a location measured by the X-ray sensor 481. Accordingly, an average amount of scattered radiation of the location of the person may be predicted.

Referring to FIG. 9, an average amount 920 of the scattered radiation of the location of a patient 921 and an average amount 930 of the scattered radiation of the location of a user 931 may be displayed in the third image 910.

Figure 10:
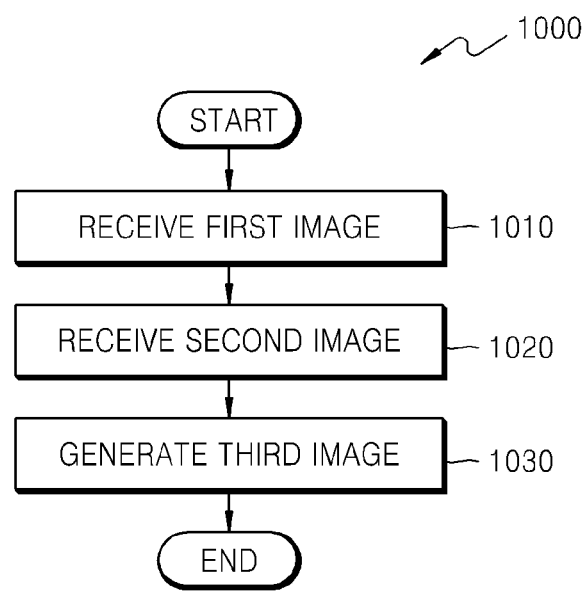
FIG. 10 is a flowchart for describing an image processing method according to an exemplary embodiment.

FIG. 10 is a flowchart for describing an image processing method 1000 according to an exemplary embodiment. Technical concepts of the image processing method 1000 are the same as those of the image processing apparatus 400 described above with reference to FIGS. 1 to 9 and may be performed by using the image processing apparatus 400. Therefore, descriptions which are the same as those given above with reference to FIGS. 1 to 9 will not be repeated here.

Referring to FIG. 10, according to the image processing method 1000, a first image of scattered radiation of X-rays existing in a predetermined space is received (operation 1010). Operation 1010 may be performed by the receiver 410. The first image may be acquired by the first camera 460.

A second image acquired by photographing the predetermined space is received (operation 1020). Operation 1020 may be performed by the receiver 410. The second image may be acquired by the second camera 470.

A third image is generated by combining the first image and the second image (operation 1030). Operation 1030 may be performed by the image processor 420.

Figure 11:
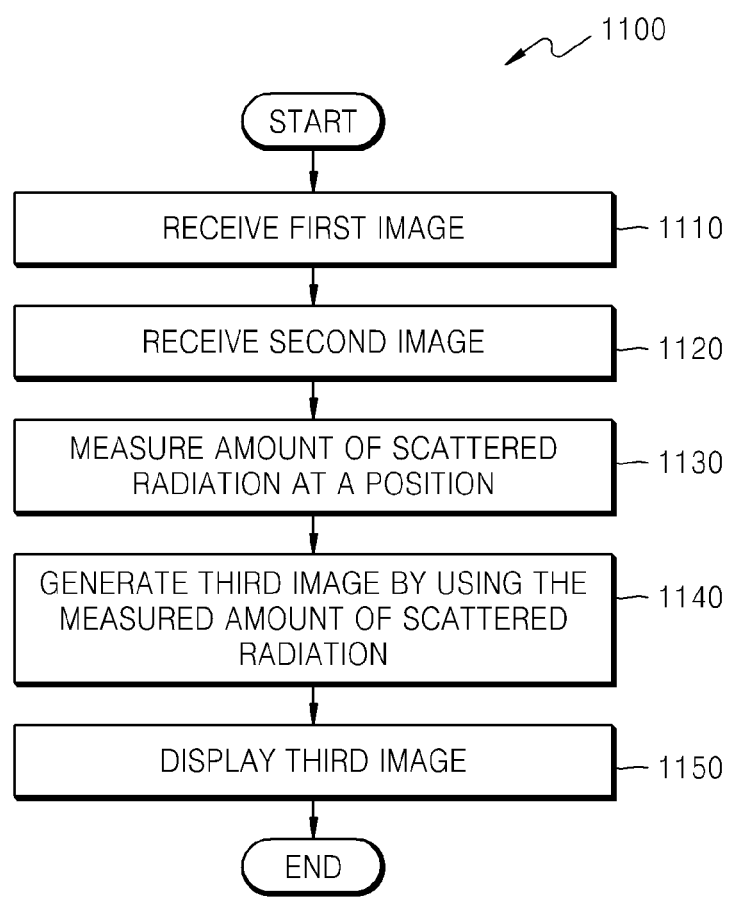
FIG. 11 is a flowchart for describing an image processing method according to another exemplary embodiment.

FIG. 11 is a flowchart for describing an image processing method according to another exemplary embodiment. Technical concepts of an image processing method 1100 are the same as those of the image processing apparatus 400 described above with reference to FIGS. 1 to 9 and may be performed by using the image processing apparatus 400. The descriptions which are the same as those given above with reference to FIGS. 1 to 10 will not be repeated here.

Referring to FIG. 11, according to the image processing method 1100, a first image of scattered radiation of X-rays existing in a predetermined space is received (operation 1110).

A second image acquired by photographing the predetermined space is received (operation 1120).

An amount of scattered radiation of X-rays at a position of the predetermined space is measured (operation 1130). Operation 1130 may be performed by the sensing unit 480. Particularly, the X-ray sensor 481 may measure the amount of scattered radiation of X-rays at one or more positions of the predetermined space.

A third image may be generated such that the amount of scattered radiation is indicated in the first image by using at least one of the measured amount of scattered radiation and the first image (operation 1140). Operation 1140 may be performed by the image processor 420.

The third image generated in operation 1140 is displayed (operation 1150). Operation 1150 may be performed by the display 430 in accordance with control of the image processor 420.

As described above, according to the image processing apparatus and image processing method of the exemplary embodiments, an image is generated such that the user may easily recognize the scattered radiation generated during radiography. As a result, the user may quickly recognize the scattered radiation. Accordingly, the user may immediately take action to prevent damage caused by scattered radiation during radiography. For example, the user may move to avoid the location where a high density of the scattered radiation exists after checking the generated third image or may stop radiography when the density of the scattered radiation continuously increases.

According to the image processing apparatus and image processing method of the exemplary embodiments, the amount of scattered radiation is estimated and displayed, and thus the user may easily recognize the absolute value of the amount of scattered radiation existing in the predetermined space.

The above-described exemplary embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.), and transmission media such as Internet transmission media.

The foregoing exemplary embodiments and advantages are merely exemplary and are not to be construed as limiting. The exemplary embodiments can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for processing an image during a medical imaging, the apparatus comprising:
   a receiver configured to receive a first image acquired by photographing scattered radiation of X-rays existing in a closed space and a second image acquired by photographing the closed space; and
   an image processor configured to generate a third image by combining the first image and the second image, wherein the third image comprises information regarding the scattered radiation of the X-rays existing in the closed space.

2. The apparatus of claim 1, wherein the image processor is configured to combine the first image and the second image by matching corresponding points of the first image and the second image in the closed space.

3. The apparatus of claim 1, further comprising a display configured to display the third image.

4. The apparatus of claim 1, further comprising:
an X-ray sensor configured to measure an amount of the scattered radiation at a position in the closed space and to transmit information regarding the amount of the scattered radiation to the receiver.

5. The apparatus of claim 4, wherein the image processor is configured to estimate an absolute value of the amount of the scattered radiation in a region of the closed space by using the information regarding the amount of scattered radiation and the first image, and to indicate the estimated absolute value in the third image.

6. The apparatus of claim 5, wherein the closed space comprises a first region having the amount of the scattered radiation greater than a reference value, and the image processor is configured to generate the third image by differently marking the first region from a second region, which is exclusive of the first region, based on the estimated absolute value, so that the first region is displayed in the third image visually different from the second region.

7. The apparatus of claim 5, wherein the image processor is configured to determine whether a first region having the amount of the scattered radiation greater than a reference value exists in the closed space based on the estimated absolute value and to output at least one of an additional image and a sound informing that the first region exists.

8. The apparatus of claim 1, further comprising:
a first camera configured to acquire the first image; and
a second camera configured to acquire the second image.

9. A method of processing an image during a medical imaging, the method comprising:
receiving a first image acquired by photographing scattered radiation of X-rays existing in a closed space;
receiving a second image acquired by photographing the closed space; and
generating a third image by combining the first image and the second image,
wherein the third image comprises information regarding the scattered radiation of the X-rays existing in the closed space.

10. The method of claim 9, wherein the generating the third image comprises:
combining the first image and the second image by matching corresponding points of the first image and the second image in the closed space.

11. The method of claim 9, further comprising:
displaying the third image.

12. The method of claim 11, further comprising:
measuring an amount of the scattered radiation at a position in the closed space.

13. The method of claim 12, wherein the generating the third image comprises:
estimating an absolute value of the amount of the scattered radiation in a region of the closed space by using the measured amount of the scattered radiation and the first image; and
indicating the estimated absolute value in the third image.

14. The method of claim 13, wherein the closed space comprises a first region having the amount of the scattered radiation greater than a reference value, and the generating the third image comprises:
generating the third image by differently marking the first region from a second region, which is exclusive of the first region, based on the estimated absolute value.

15. The method of claim 13, further comprising:
determining whether a first region, in which the amount of scattered radiation exceeds a reference value, exists in the closed space based on the estimated absolute value; and
outputting at least one of an additional image and a sound informing about an existence of the first region in response to a determination that the first region exists.

16. An X-ray apparatus comprising:
an X-ray device which is disposed in a closed space, and configured to irradiate X-rays to an object and acquire an X-ray image of the object;
an X-ray camera configured to photograph scattered radiation of the X-rays existing in the closed space;
a camera configured to photograph the closed space;
an image processor configured to generate a third image by combining a first image acquired by the X-ray camera and a second image acquired by the camera; and
a display configured to display the third image,
wherein the third image comprises information regarding the scattered radiation of the X-rays existing in the closed space.

17. The apparatus of claim 16, wherein the X-ray device comprises:
a high voltage generator configured to generate a high voltage;
an X-ray irradiation unit configured to generate the X-rays by using the high voltage supplied from the high voltage generator and to irradiate the X-rays to the object; and
a detector configured to detect the X-rays having passed through the object.

18. The method of claim 9, further comprising:
measuring an amount of the scattered radiation at a location in the closed space; and
controlling a sound output unit configured to output a warning sound when the measured amount of scattered radiation at the location exceeds a reference value.

19. The method of claim 9, further comprising:
measuring an amount of the scattered radiation at one or more locations in the closed space; and
controlling a display configured to display a warning message in the third image when the measured amount of the scattered radiation at the one or more the locations is greater than a reference value.

20. The apparatus of claim 1, wherein the image processor is configured to output any one or any combination of a warning image and a warning sound when a region having an amount of the scattered radiation that is greater than a reference value exists in the closed space.

* * * * *